United States Patent [19]

Boquet

[11] Patent Number: 5,352,609
[45] Date of Patent: Oct. 4, 1994

[54] CARTRIDGE, APPARATUS, AND METHOD FOR PREPARING PURIFIED NUCLEIC ACIDS FROM A CELL SAMPLE

[75] Inventor: Jean Boquet, Le-Perray-en-Yvelines, France

[73] Assignee: Bertin & Cie, Plaisir Cedex, France

[21] Appl. No.: 977,427

[22] PCT Filed: Jul. 6, 1992

[86] PCT No.: PCT/FR92/00646
  § 371 Date: Feb. 23, 1993
  § 102(e) Date: Feb. 23, 1993

[87] PCT Pub. No.: WO93/01312
  PCT Pub. Date: Jan. 21, 1993

[30] Foreign Application Priority Data

Jul. 9, 1991 [FR] France .................. 91 08579

[51] Int. Cl.$^5$ .............. B01D 63/00; C12Q 1/68; C12N 1/06; C12N 1/08
[52] U.S. Cl. .............. 435/270; 210/321.64; 210/321.71; 210/321.75; 435/259; 435/6; 436/178; 536/25.4; 536/25.41
[58] Field of Search ........ 435/267, 270, 272, 287, 435/803, 820, 6, 259, 264, 274; 436/63, 175, 177, 178; 422/68.1, 101; 210/321.64, 321.71, 321.72, 321.75; 536/25.4, 25.41

[56] References Cited

U.S. PATENT DOCUMENTS

| | | | |
|---|---|---|---|
| 3,684,097 | 8/1972 | Mathewson et al. | 210/321.75 X |
| 3,976,576 | 8/1976 | Jacobsen et al. | 210/321 |
| 4,540,492 | 10/1985 | Kessler | 210/321.75 X |
| 4,787,963 | 11/1988 | MacConnell | 435/6 |
| 4,849,102 | 7/1989 | Latour et al. | 210/321.64 |
| 4,861,485 | 8/1989 | Fecondini | 210/321.64 X |
| 4,921,952 | 5/1990 | Longmire et al. | 536/27 |
| 5,015,388 | 5/1991 | Pusineri et aL. | 210/321.64 |
| 5,187,083 | 2/1993 | Mullis | 435/91 |
| 5,196,352 | 3/1993 | Siekierka et al. | 436/501 |

FOREIGN PATENT DOCUMENTS

| | | |
|---|---|---|
| 245945 | 11/1987 | European Pat. Off. . |
| 431905 | 6/1991 | European Pat. Off. . |
| 2039050 | 2/1972 | Fed. Rep. of Germany . |
| WO90/15148 | 12/1990 | PCT Int'l Appl. . |

*Primary Examiner*—Robert J. Warden
*Assistant Examiner*—Robert Carpenter
*Attorney, Agent, or Firm*—Bell, Seltzer, Park & Gibson

[57] ABSTRACT

A cartridge for preparing nucleic acids such as DNA from cells comprises two end rings (14) enabling it to be mounted in sealed manner in a tube (10), two dialysis membranes (16) delimiting a dialysis enclosure (18) between them, a filter (20) for retaining cell nuclei dividing said enclosure (18) into two separate compartments, and means (24) for feeding substances into one of the compartments, means (26) for extracting substances from the other compartments, and means (28, 30) for feeding a dialysis liquid into the tube outside the cartridge, or for causing it to flow therethrough. The invention also provides apparatus, and a method using said cartridge.

15 Claims, 3 Drawing Sheets

CARTRIDGE, APPARATUS, AND METHOD FOR PREPARING PURIFIED NUCLEIC ACIDS FROM A CELL SAMPLE

The invention relates to a cartridge for extracting and purifying nucleic acids, in particular genome DNA, from a sample of blood, of tissue cells, or of culture cells, and also to apparatus and a method making use of said cartridge.

Conventional methods for extracting DNA from cells generally consist in total lysis of the cells, in degradation of the proteins by means of enzymes, in removing the degraded proteins and the lipids by means of phenol and chloroform, in precipitating the DNA by means of ethanol, and then in putting the extracted DNA back into suspension.

To extract DNA from the blood of mammals, the treatment comprises lysis of the red corpuscles and of the plasma membranes of the white corpuscles, leaving the nuclei of the white corpuscles intact, and then separating out said nuclei by centrifuging and subsequently treating them as described above.

With solid tissue, the tissue is broken up and homogenized in an appropriate solution before being subjected to the above-described treatment.

The above treatments are lengthy and fiddly and they lend themselves poorly to extracting genome DNA from a large number of cell samples. In addition they require toxic solvents to be handled such as phenol and chloroform.

Simpler methods have already been proposed (see for example "Nucleic Acids Research" Vol. 17, No. 20, 1989, page 8390) essentially consisting in cell lysis, in isolating the nuclei by centrifuging, in nucleus lysis, and in degrading the proteins with a mixture of PLB and of K proteinase, while avoiding the use of solvents such as phenol and chloroform.

An essential object of the present invention is to provide a cartridge for extracting and purifying nucleic acids such as genome DNA from a cell sample, enabling the extraction of DNA to be further simplified by eliminating the centrifuging separation operations used in the prior art, and also eliminating extraction by means of organic solvents, precipitation of the DNA, and putting it back into suspension (a step which is often very time consuming).

Another object of the invention is to provide apparatus and a method for extracting and purifying nucleic acids such as genome DNA, making use of said cartridge.

To this end, the invention provides a cartridge comprising a dialysis enclosure in particular for purifying nucleic acids, and inlet and outlet means for admitting and extracting substances into and out from the dialysis enclosure, the cartridge being characterized in that it comprises a thin elongate plane support having a central slot, with dialysis membranes being fixed on two faces thereof with the dialysis enclosure being defined between them, and two end rings which are mounted on longitudinally opposite ends of said support, each including a through duct that opens out into the dialysis enclosure.

Such a cartridge can be made having dimensions that enable it to be mounted in a standard tube of a conventional device for treating biological samples, e.g. a carousel type device as is widely used in biological laboratories.

Advantageously, the cartridge of the invention comprises a filter for retaining the cell nuclei and carried by the support to separate the dialysis enclosure into two separate compartments into which the through ducts of said rings open out on respective opposite sides of the filter.

The above-mentioned filter may, for example, be a polyester film having very fine mesh size with dimensions of the order of 1 micrometer.

The presence of this filter in the dialysis enclosure of the cartridge makes it possible to avoid the conventional operations of separating out the nuclei by centrifuging, because the cell nuclei are retained and fixed selectively on the filter when the lysed cells are caused to flow in the dialysis enclosure through the filter.

In a preferred embodiment of the invention, the above-mentioned support is made up of two superposed rectangular frames, each frame having a substantially axial groove on the inside-face of one of its short sides, which groove has one end opening out into the dialysis enclosure and another end opening out into the through duct of the corresponding ring.

The above-mentioned filter is fixed between the two superposed frames in such a manner that the through ducts of the end rings open out on respective opposite sides of the filter.

According to another characteristic of the invention, each ring includes at one of its end faces a transverse groove for receiving a short side of the above-mentioned frame and into which the through duct of the ring opens out facing the axial groove formed in said short side of the frame.

The other end face of the ring includes a septum or cylindrical cavity for receiving a disk of elastomer material having a self-closing small-diameter axial bore. The through duct of the ring is formed through the bottom of said cavity.

The invention also provides apparatus for extracting and purifying nucleic acids from a cell sample by means of a cartridge of the above-specified type, the apparatus being characterized in that it comprises at least one tube in which said cartridge is mounted in sealed manner via its end rings, means for feeding a dialysis liquid into the tube outside the cartridge, or for causing it to flow therethrough, link means connecting the through ducts of the end rings selectively to means for extraction by blowing and/or suction, and to means for feeding a sample to be treated, for feeding a reagent, or for feeding washing substances.

The extraction and purification of nucleic acids, in particular DNA, can be performed entirely within the cartridge placed in a tube of the apparatus, without it being necessary to remove said tube or said cartridge from the apparatus, e.g. for operations of separation by centrifuging.

Advantageously, said cartridge is disposed in the tube between two semi-cylindrical parts enabling the free inside volume of the tube to be reduced and including ducts through which the dialysis liquid can flow.

By its very structure, the cartridge is of low cost and may thus be discarded after use, thereby avoiding any risk of contamination or pollution from one sample to another.

The invention also provides a method of preparing purified nucleic acids from a cell sample, by lysis of the cell nuclei, by degrading proteins, and by purifying the nucleic acids by dialysis, the method being characterized in that it essentially comprises:

a step of separating out and fixing the nuclei on a filter placed in a dialysis enclosure;

a step of in situ lysis of the nuclei fixed on the filter, and including degradation of unwanted proteins and nucleic acids; and a final step of in situ dialysis to eliminate from said enclosure any constituents other than the looked-for nucleic acids.

Advantageously, the method also includes a prior step of in situ lysis of the cells inside the dialysis enclosure.

In addition, the fixing of the nuclei on the above-mentioned filter in the dialysis enclosure makes it possible to subject said nuclei to successive washes using buffers suitable for eliminating lipids, ribosomes that may remain attached to the cell membranes, or molecules internal to the nuclei other than the nucleic acids to be purified.

Such a method is obvious to implement in the cartridge of the invention without requiring the cartridge to be handled between two steps of the method.

BRIEF DESCRIPTION OF THE DRAWINGS

The invention will be better understood and other characteristics, details, and advantages thereof will appear more clearly on reading the following description given by way of example and made with reference to the accompanying drawings, in which.

Figure 1:
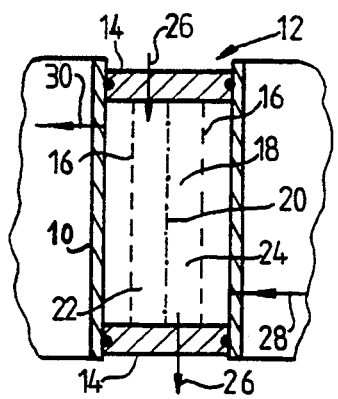
FIG. 1 is a diagram showing the principle of the invention.
Figure 3:
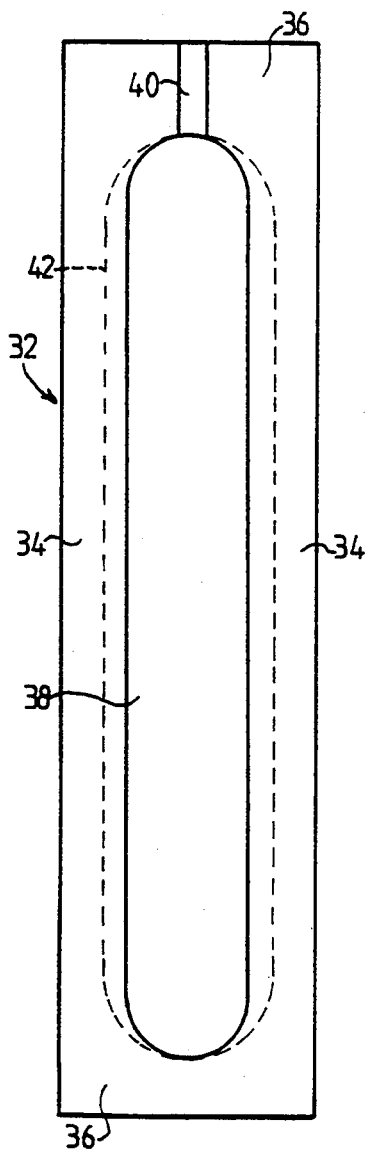
FIG. 3 is an elevation view of a filter and membrane support frame.
Figure 2:
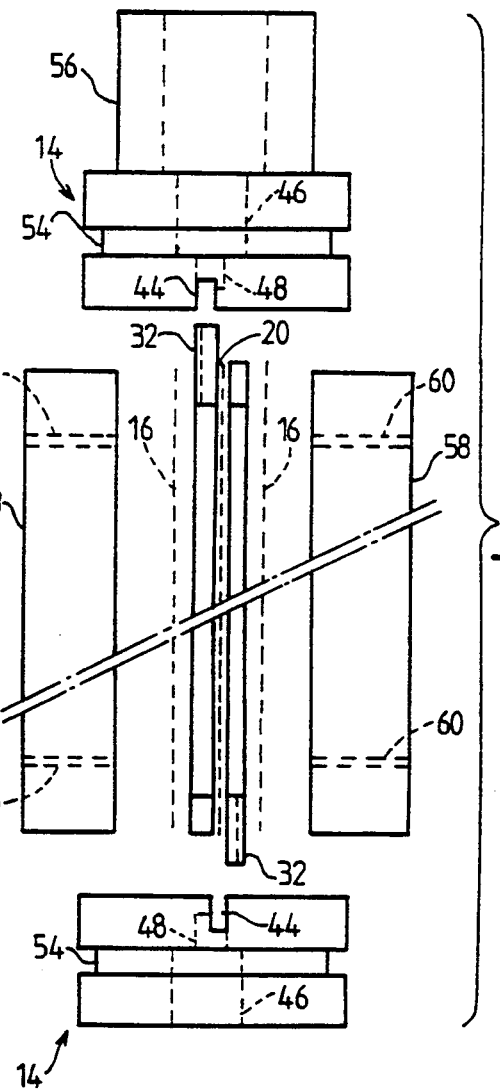
FIG. 2 is an exploded view of the various components of an extraction cartridge in accordance with the invention.
Figure 4:
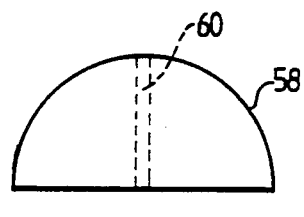
FIG. 4 is a plan view of a semi-cylindrical volume-reducing part.

Reference is made initially to FIG. 1 which shows the principle of the invention diagrammatically.

In this figure, reference 10 designates a cylindrical tube that is open at both ends, and in which a cartridge 12 of the invention is mounted in sealed manner, the cartridge comprising two end rings 14 having disposed therebetween two dialysis membranes 16 which together define a closed dialysis enclosure 18, and a filter 20 which divides the dialysis enclosure 18 into two separate compartments 22 and 24. The top ring 14 includes a duct 26 for feeding a sample and other substances into the dialysis enclosure, specifically into the compartment 22, while the bottom ring 14 includes an outlet duct 26 for substances and that opens out into the other compartment 24 of the dialysis enclosure. Finally, the tube 10 includes ducts 28 and 30 respectively for feeding and for extracting a dialysis liquid, which ducts open out into the tube outside the dialysis enclosure 18 delimited by the membranes 16.

Operation is as follows:

The sample to be treated, e.g. blood, is fed together with a conventional substance for controlled lysis of the corpuscles into the dialysis enclosure 18 via the duct 26 through the top ring 14, and subsequently leaves said dialysis enclosure 18 via the duct 26 through the bottom ring 14, after passing through the filter 20. This filter is constituted, for example, by a thin polyester film, e.g. about 1 micrometer thick, having a very fine mesh with dimensions of the order of 1 micrometer, thereby retaining and fixing the nuclei of the lysed corpuscles.

After washing by causing one or more suitable buffers to flow through the enclosure 18, the nuclei fixed to the filter 20 are subjected to lysis, the RNAs are degraded, e.g. by means of RNases, and the proteins are degraded, e.g. by means of K proteinase, the DNA present in the enclosure 18 is purified by dialysis in the tube 10, and thereafter the DNA is extracted from the enclosure 18, e.g. by blowing air along the upper duct 26 and/or by suction via the lower duct 26.

Reference is now made to FIGS. 2 to 5 which show a preferred embodiment of the cartridge of the invention.

As already mentioned, this cartridge comprises two end rings 14, and two dialysis membranes 16 fixed on a narrow plane support that also carries the filter 20. The support for the membranes 16 and for the filter 20 is constituted by two identical superposed rectangular frames 32, one of which is shown in elevation and on a larger scale in FIG. 3. Each frame 32 is made of a synthetic material or of a composite material based on fiberglass, and comprises two longitudinal long sides 34 interconnected by two transverse short sides 36 so as to define an elongate central slot 38. One of the short sides 26 of the frame 32 includes a substantially axial groove 40 in its inner face, i.e. its face that is pressed against the other frame 32, with the ends of said groove opening to the outside of the frame and to the slot 38 respectively. On the other face of the frame 32, i.e. the face for receiving a membrane 16, the edges of the slot 38 are chamfered as shown in dashed lines referenced 42 in FIG. 3.

The two frames 32 are superposed while being placed head-to-tail, the filter 20 being fixed by being glued around its periphery to the inside face of one of the frames, and the other frame is then glued onto the first so that their slots 38 are in alignment while nevertheless being separated from each other by the filter 20. The dialysis membranes 16 are then glued via their peripheries onto the outside faces of the frames 32.

The short transverse sides 36 of the frames 32 that include the above-mentioned grooves 40 are wider than the other short sides 36 of said frames, such that in the configuration obtained by assembling two frames together, the short side 36 of one frame that includes a groove 40 projects outwardly beyond the other short side 36 of the other frame.

Each ring 14 is generally cylindrical in shape and at its end facing the frames 32 it includes a diametral groove 44 for receiving the short side 36 of a frame having a groove 30 formed therein.

Figure 5:
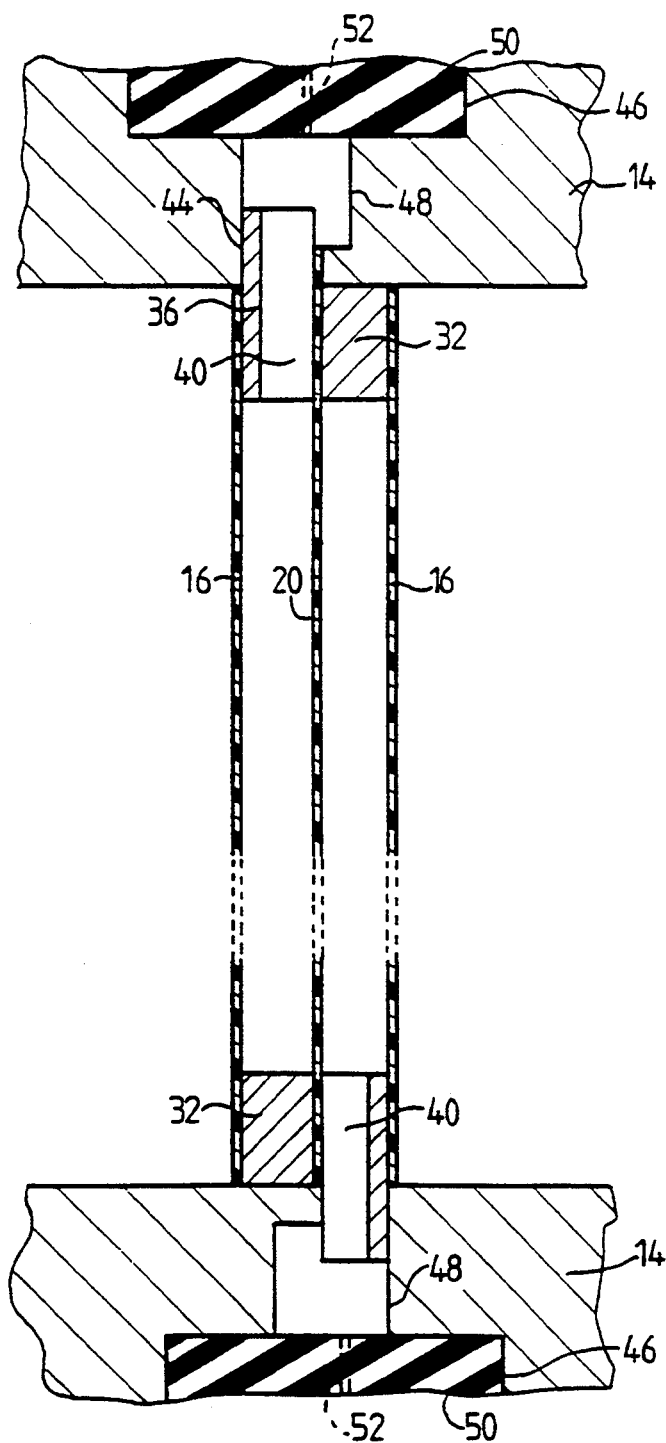
FIG. 5 is a fragmentary and diagrammatic view on a larger scale and in axial section of an extraction cartridge.

The opposite end of each ring 14 has a cylindrical cavity 46 whose bottom is at a distance from the bottom of the groove 44 and which communicates with said groove via a small diameter bore 48 (e.g. 2 mm diameter). The cavity 46 in each ring 14 is intended to receive a "septum" or disk 50 of elastomer that includes a very fine axial bore 52 that is self-closing, and that opens out into the above-mentioned bore 48 (FIG. 5).

Each ring 14 also includes a peripheral groove 54 enabling a sealing ring to be installed.

It may be observed that the top ring 14 is extended upwards by a cylindrical skirt 56 enabling a few drops of liquid to be collected during connection and disconnection of the extraction cartridge to means for feeding the substance or the reagent, thereby avoiding polluting or contaminating surrounding surfaces.

Finally, it is possible to provide two complementary parts 58 that are semi-cylindrical in shape and that may be solid parts made of a suitable plastic, and including through passages 60. These parts 58 are intended to be disposed on either side of the frames 32 of the extraction cartridge when inside a tube 10 so as to reduce the empty inside volume in said tube, thereby reducing the volume of dialysis liquid that must be fed to the inside of the tube in order to fill it.

The cartridge shown in FIGS. 2 to 5 is used as follows:

When mounted in sealed manner in a cylindrical tube 10, as shown diagrammatically in FIG. 1, an injection needle is pushed into the bore 52 of the disk 50 or "septum" of the top ring in order to feed a sample, a reagent, or a washing liquid into the enclosure formed by the membranes 16 fixed on the frames 32. The substance injected by the needle passes through the bore 48 of the top ring 14, the groove 40 in the top transverse side of a frame 42, and thus fills the dialysis enclosure, passing through the filter 20. To extract said substance, it suffices to push an injection needle into the bore 52 of the disk 50 or septum of the bottom ring 14 and to suck out the substance contained in the dialysis enclosure.

Figure 6:
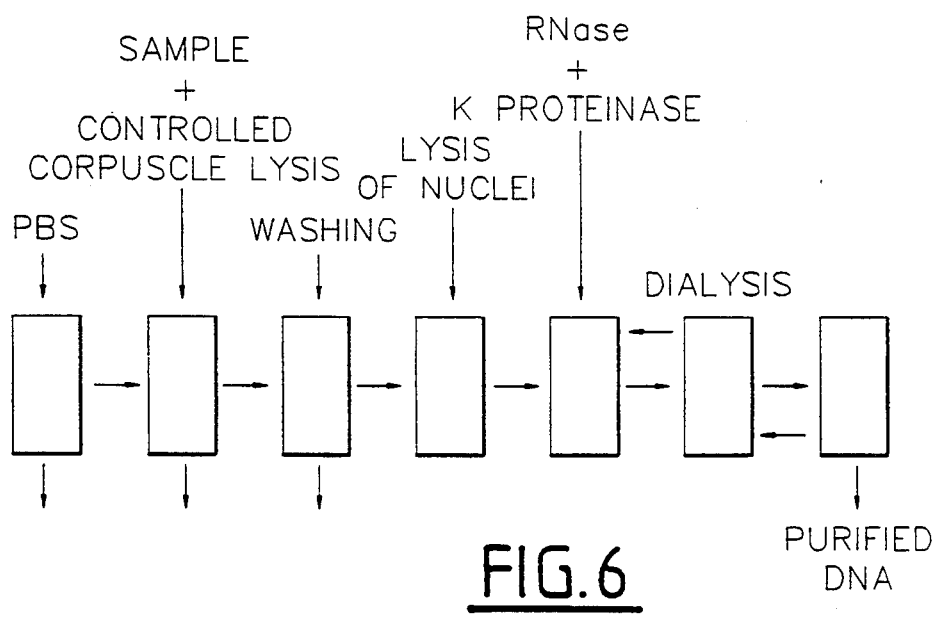
FIG. 6 is a diagram showing the essential operations of the method of the invention for extracting DNA.

In order to extract genome DNA from a blood sample, the following procedure is followed, as shown diagrammatically in FIG. 6:

Initially, the cartridge is washed by injecting and then extracting 10 ml of PBS. Thereafter a 10 ml sample of blood mixed with 10 ml of a corpuscle lysis substance is inserted into the cartridge, where the lysis substance is a mixture of sucrose and of Triton, for example, as described in the above-mentioned article in the journal "Nucleic Acids Research", and the mixture is allowed to incubate for 1½ hours at 4° C. The mixture is then extracted from the cartridge, with the nuclei of the corpuscles remaining attached to the filter 20. Thereafter, two PBS washing operations are performed (10 ml each time) and then 1.5 ml of a substance for nucleus lysis is injected into the cartridge together with 0.5 ml of K proteinase. The cartridge is then incubated for 1 hour at 55° C.

Thereafter, dialysis is performed for several hours at about 60° C. by feeding a dialysis liquid into the tube 10 outside the dialysis enclosure delimited by the membranes 16 of the cartridge so as to purify the DNA present in said cartridge and so as to remove all waste, after which the DNA is extracted by blowing and/or sucking in the dialysis enclosure.

The high temperature at which dialysis takes place enables the duration of said operation to be greatly reduced, since it would be about 20 hours at ambient temperature.

DNA can also be extracted from culture cells or from tissue that has previously been broken up and homogenized. In all cases, it is advantageous to retain and fix the nuclei on the filter 20 of the cartridge, so as subsequently to perform successive washing operations using suitable buffers serving, in particular, to eliminate lipids, ribosomes still attached to the nuclei, and nuclear proteins, including a portion of the histones.

For example, filter washing may begin with a solution containing Triton x-100 at 1%. The remaining blood products are then clearly detached from the filter and the nuclei are completely separated from their outer lipid membranes. A portion of the histones is also extracted.

Thereafter, by washing at high ionic force (NaCl at 2M), most of the remaining RNA is removed from the nuclei, together with certain proteins.

Thereafter, as described above, a substance for lysis of the nuclei is injected into the cartridge together with 0.5 ml of K proteinase, and the remaining DNA is then purified by dialysis. The washing operations described above make it possible to obtain DNA of greater purity for certain types of cell.

The invention is also applicable to extracting and purifying RNAs by degradation and elimination of DNAs. Since RNAs, it is necessary to use dialysis membranes having smaller pores, thereby making dialysis less efficient and purification less good. DNA can be degraded by means of enzymes by using DNases instead of RNases, or by mechanical action (e.g. by ultrasonic shear).

I claim:

1. A cartridge for preparing purified nucleic acids from cells, the cartridge comprising a dialysis enclosure, a filter provided in the dialysis enclosure for separating it into two separate compartments, the filter being in a material adapted for retaining cell nuclei, and inlet and outlet means for admitting and extracting substances into and out from the dialysis enclosure, said enclosure comprising a elongate plane support having a central slot and two outer faces, two dialysis membranes fixed on the outer faces of the support for defining the dialysis enclosure between them, and two end rings mounted on longitudinally opposite ends of the support and each comprising a through duct that opens out into the dialysis enclosure, the through duct of one of the end rings opening out on a side of the filter and the through duct of the other end ring opening out on an opposite side of the filter.

2. A cartridge according to claim 1, wherein the filter is a polyester film having mesh size of about 1 micrometer.

3. A cartridge according to claim 1, wherein said support is made up of two superposed rectangular frames, each frame having an inside and an outside face, a substantially axial groove on the inside face of one of the short sides of said rectangular frames, which groove has one end opening out into the dialysis enclosure and another end opening out into the through duct of one of said end rings.

4. A cartridge according to claim 3, wherein the rectangular frames and the end rings are made of a synthetic material or of a composite material based on glass fiber.

5. A cartridge according to claim 3, wherein the inside edges of said slot of each frame are chamfered adjacent to the outside face of the frame on which a dialysis membrane is fixed.

6. A cartridge according to claim 3, wherein the filter is fixed between the two superposed frames.

7. A cartridge according to claim 3, wherein each ring includes a transverse groove for receiving a short side of one of said frames and into which the through duct of the end ring opens out facing the axial groove formed in said short side of the frame.

8. A cartridge according to claim 7, wherein each end ring includes a cylindrical cavity at its outer end for receiving a disk of elastomer having a self-sealing axial bore, and the through duct of the end ring is formed through the bottom of said cavity.

9. A cartridge according to claim 1, wherein each ring includes a peripheral annular sealing ring.

10. Apparatus for preparing purified nucleic acids from cells the apparatus comprising the cartridge of claim 1 at least one tube in which said cartridge is mounted in sealed manner via its end rings, means for feeding a dialysis liquid into the tube outside the cartridge and for causing it to flow therethrough, link means for connecting the through ducts of the end rings selectively to means for extraction by at least one of blowing and suction, and to means for feeding a sample to be treated, means for feeding a reagent, and means for feeding washing substances.

11. Apparatus according to claim 10, wherein said cartridge is disposed in the tube between two semi-cylindrical parts including ducts through which the dialysis liquid can flow.

12. A method of preparing purified nucleic acids from cells, by lysis of the cell nuclei, by degrading proteins, and by purifying the nucleic acids by dialysis, comprising:
- a step of fixing the nuclei on a filter placed in a dialysis enclosure;
- a step of in situ lysis of the nuclei fixed on the filter, and including degradation of proteins and nucleic acids other than looked-for nucleic acids;
- a final step of in situ dialysis to eliminate from said enclosure any constituents other than the looked-for nucleic acids.

13. A method according to claim 12, further comprising a prior step of in situ lysis of the cells inside the dialysis enclosure.

14. A method according to claim 12, further comprising successive steps of washing the nuclei fixed on the filter using buffers suitable for eliminating lipids, ribosomes that have remained attached to the nuclei, and internal molecules of the nuclei other than the looked-for nucleic acids.

15. A method according to claim 12, wherein the final dialysis step is performed at about 60° C.

* * * * *